United States Patent [19]

Jones

[11] Patent Number: 4,896,085
[45] Date of Patent: Jan. 23, 1990

[54] IMPULSE ACTUATOR SYSTEM

[75] Inventor: J. Paul Jones, Chester Springs, Pa.

[73] Assignee: Patent Research and Development Corp., Exton, Pa.

[21] Appl. No.: 219,436

[22] Filed: Jul. 15, 1988

[51] Int. Cl.⁴ .............................................. H02P 3/08
[52] U.S. Cl. .................................... 318/560; 318/475; 318/491; 318/541; 222/333; 604/151; 604/152
[58] Field of Search ............. 318/560, 135, 685, 687, 318/362, 491, 541, 681, 653, 446, 442, 266, 443, 475, 561, 568, 372, 468, 467, 466; 604/8, 9, 67, 131, 135, 151, 154, 155, 152, 183, 185, 207, 222, 224; 222/1, 63, 333, 390; 128/214 F, 214 E, DIG. 25; 417/22, 63, 201, 374, 391, 477, 479, 540, 542, 416

[56] References Cited

U.S. PATENT DOCUMENTS

| | | | |
|---|---|---|---|
| 3,762,411 | 10/1973 | Lloyd et al. | 604/151 |
| 3,841,331 | 10/1974 | Wilder et al. | 604/152 |
| 3,931,914 | 1/1976 | Hosaka et al. | 222/333 X |
| 4,320,317 | 3/1982 | Bowey | 318/475 X |
| 4,322,201 | 3/1982 | Archibald | 604/152 X |
| 4,396,385 | 8/1983 | Kelly et al. | 604/152 |
| 4,446,988 | 5/1984 | Chronis | 222/333 X |
| 4,474,309 | 10/1984 | Soloman | 318/685 X |
| 4,478,355 | 10/1984 | Houman | 222/63 X |
| 4,656,687 | 4/1987 | Wei | 417/201 X |
| 4,760,318 | 7/1988 | Jones | 318/362 |

Primary Examiner—William M. Shoop, Jr.
Assistant Examiner—Paul Ip

[57] ABSTRACT

A silent, high torque, impulse actuator system for low average power devices. The system incorporates a typical small three pole D.C. motor which has been modified to allow quick electrical conversion, with unipolar switching circuitry, from conventional rotation, to silent magnetic braking at a stop position; and then to a normally OFF condition.

The high efficiency of this intermittent drive system is enhanced by the unique combination of being normally off between actuations; the high efficiency of the D.C. motor during start conditions; and the use of a round cam to provide a cosine power stroke that utilizes the inertia of the motor rotor to maximum mechanical advantage.

2 Claims, 4 Drawing Sheets

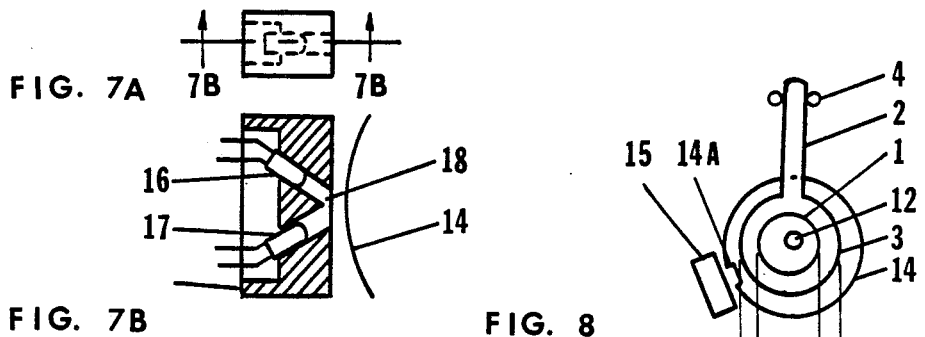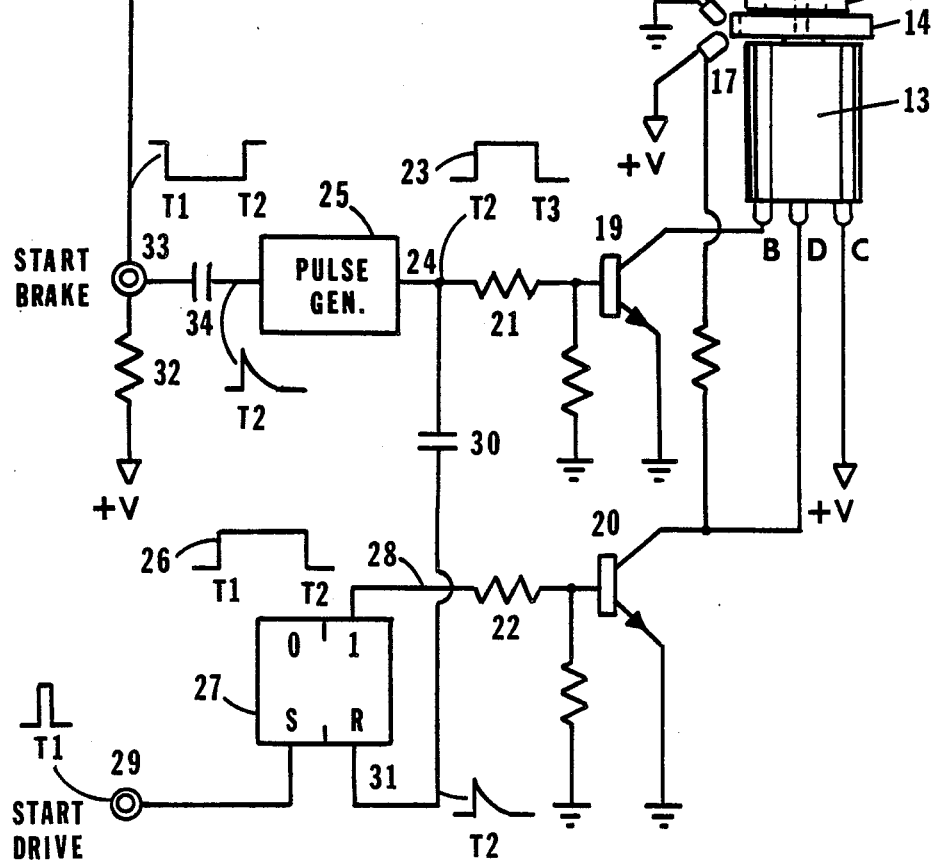

IMPULSE ACTUATOR SYSTEM

This invention relates in general to actuating devices and, in particular, to an Impulse Actuator System which is based on a conventional three pole D.C. Motor, which has an added brush that is electrically switched to provide a silent magnetic braking to a stop position at the end of a single rotation; and which drives a rotary cam through a single 360 degree rotation for each impulse. The actual modification and operation of the D.C. Motor maybe referenced in our copending application, Ser. No. 917,005, now U.S. Pat. No. 4,760,318 for an Intermittant Single Rotation Motor Actuator. The description in U.S. Pat. No. 4,760,318 is incorporated herein by reference. The new system is particularly adaptable to miniature D.C. motors, which can, with this invention, be used to drive impulse actuated mechanisms with low average power; such as required in many small battery operated medical devices.

The new Actuator System includes a silent cosine cam, which delivers peak output at 180 degrees, and a detection means, which senses the rotation of the drive shaft at 270 to 300 degrees, to establish the braking and stop positions, regardless of variable loading effects on the motor.

BACKGROUND

As more and more electronic devices are made with digital controls; and as the devices become smaller and smaller, the need for impulse actuators that can operate on low average power has steadily increased. There are very few basic mechanisms that can efficiently translate an electrical impulse into linear mechanical motion. A requirement that the motion be silent, makes the design even more difficult; and eliminates most of the electromechanical devices now being used.

The most common electrical device for deriving linear motion is the solenoid coil, with a moving core plug. It is, however, very inefficient because of the large starting air gap involved; and the core of the solenoid makes a great deal of noise when it reaches the end of travel. The movement of the core is very quick but with very little starting force; consiquently, it cannot store its force over a period of time, and transfer the energy slowly into a high inertia load.

There are rotary solenoids which translate a lateral core motion, through balls in a sloped race, into a rotational motion, of the order of 20 to 30 degrees. This type does have the ability to store energy during the rotation; however, it must return to the starting position by spring loading, which robs it of useable power during the power stroke; and this type of rotary solenoid is also very noisy.

It is, therefore, one object of this invention to provide an efficient D.C.Impulse Actuator System which, with an added brush contact to the armature of a small D.C. motor and suitable drive circuitry, can be used as a relatively silent single turn rotary actuator; which, with the use of a suitable 360 degree rotating cam, can produce a single in line drive motion from each electrical start pulse.

Most magnetically actuated devices at present, such as the solenoid and relay type mechanisms, have power curves that are inversely proportional (by square law) to the size of the magnetic air gap. Consiquently, the start-up or stall power drops off quickly as the required distance of movement is increased.

It is, therefore, another object of the invention to utilize the efficient design of a conventional D.C. motor, which has the advantage (1) a very small air gap between the armature poles and the field magnets; and (2) an efficient build up of inertia as the armature speed builds up; with a round cam which delivers maximum output at 180 degrees rotation; and utilizes the energy that is stored in the armature to drive a load over a relatively long portion of the cycle.

In many cases, such as in miniature pumps, the required power to the pump builds up as the actuating stroke nears its end of travel—much as with the piston of a car motor as it approaches top dead center.

It is yet another object of this invention to provide an integrated Impulse Drive System that is easily adaptable to miniature devices, and that combines the characteristics of the single turn D.C. Motor Actuator, and the cosine characteristic of a round rotating cam, as the matched elements of a silent, single stroke, in-line actuator.

One of the primary advantages of impulse actuated mechanisms, and particularly when the impulses are needed at relatively slow rates, is the low average power requirement; because the power can be completely off between impulses. This requirement is especially acute when the equipment incorporating the drive element is to be portable and battery operated. When using battery operated equipment it is also desirable to have the mechanical element self regulating, so that it will not be necessary to use power wasting series regulation to overcome the natural decay of voltage as the batteries are being used.

It is, therefore, an important object of this system invention to have integrated control circuitry that is normally off between impulses, and which has the means to detect the position of the single turn motor and its associated rotating cam at the end-of-drive point, to signal the beginning of the braking cycle; this type of feedback permitting a decay in battery voltage, as well as normal variations in the load conditions.

The combined features of the Impulse Actuator System, based on the Motor Actuator in copending application Ser. No. 917,005, will be more completely outlined in the following drawings, and operational description:

FIGS. 1 and 2 show the basic mechanical elements of the Impulse Drive System, as it it used in a typical fluid pump system.

FIGS. 3 thru 6 show the circular motor cam, the associated Cam Bearing and Shaft, and the shaft guide pins. The four figures depict the action of the cam driven ring bearing and shaft, at each 90 degree point; when the system is used for driving a tubular pump section, as shown in FIGS. 1 and 2.

FIGS. 7A, 7B show the details of the Optical Timing Disc Sensor Assembly; with the solid state emitter and detector diodes.

FIG. 8 shows a vertical projection of the Motor Cam, Cam Bearing Shaft, Motor Timing Disc, and Optical Timing Disc Sensor.

FIG. 9 shows the Intermittent Drive and Braking Circuit; with the circuit connections shown in relation to the associated motor, motor cam, motor timing disc, and angle sensing elements.

SYSTEM OPERATION

The Impulse Actuator System is built around the unique adaptation of a three pole D.C. motor, as shown in our copending application, Ser. No. 917,005; which describes and claims the internal modification of a standard D.C. motor, to enable it to be externally switched from a standard rotational mode of operation to an efficient and silent magnetic brake.

What is especially important about the motor control system is that it does not require any reversal of voltage polarities; which always has attendant problems of crossover shorting of the momentary high current circuitry, during the polarity transition. Circuitry that can accomplish double pole polarity switching is also very complex and relatively expensive compared to the unipolar control circuitry required in this new Impulse Actuator System.

Of all magnetically operated actuator mechanisms, there are few that can compare, in efficiency, to a D.C. Motor during the first 360 degree rotation, after being turned on. With the advantage of a very small air gaps between the rotor and the magnetic field armature, and the first rotation near stall conditions, the maximum power can be obtained. This is because the back EMF that is normally created at high rotational speeds is not yet present, and the motor has not yet developed any substantial hysteresis losses.

Figure 1:
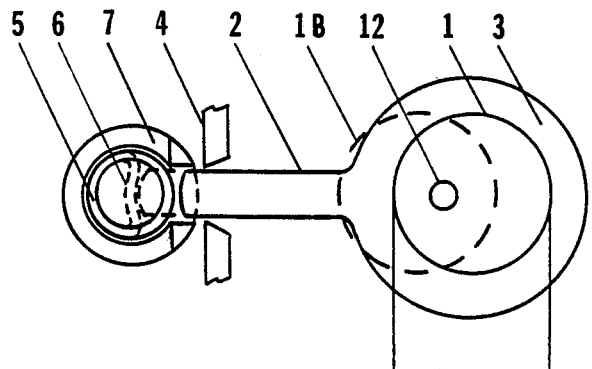
Figure 2:
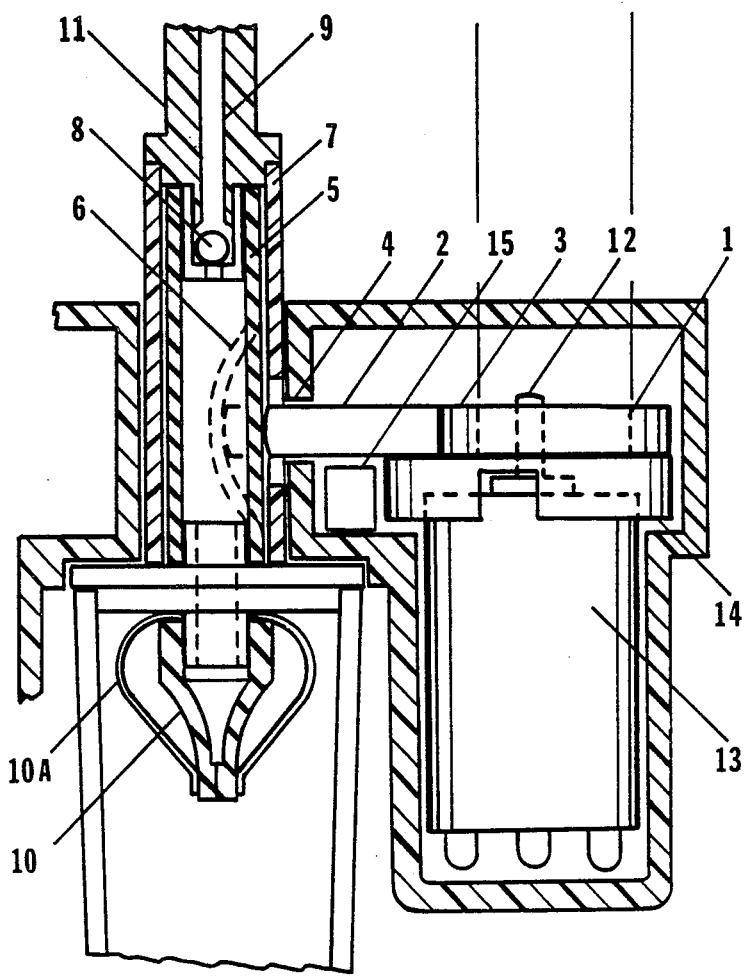

Furthermore, if the full 360 degree rotation of the D.C. motor is to be utilized for driving relatively slow impulse actuated devices, such as the small fluid pump shown in FIGS. 1 and 2, the inertia that is built up in the motor rotor can be efficiently used over a substantial portion of the single rotation and all the rotor inertia can be turned into useful work.

Most of the loads that Impulse Actuators must drive, such as a spring movement or a pump, become more demanding of force during the peak part of the stroke. Therefore, it is an optimum condition for a 360 degree actuator motor to store the increasing momentum of the motor rotor thru the first 120 degrees of rotation, and then deliver its peak power thru the 120 to 240 degree (180 degree center) portion of the full 360 degree rotation.

The perfect mechanical match for this optimum loading requirement is the action of a round, off-center cam. A round cam, such as shown in FIGS. 3 thru 6, produces a Bearing Shaft movement that is rapidly slowing after 120 degrees, while conversely building up peak force as it passes thru the maximum point of movement at 180 degrees, as in a cosine curve.

Figure 10A:
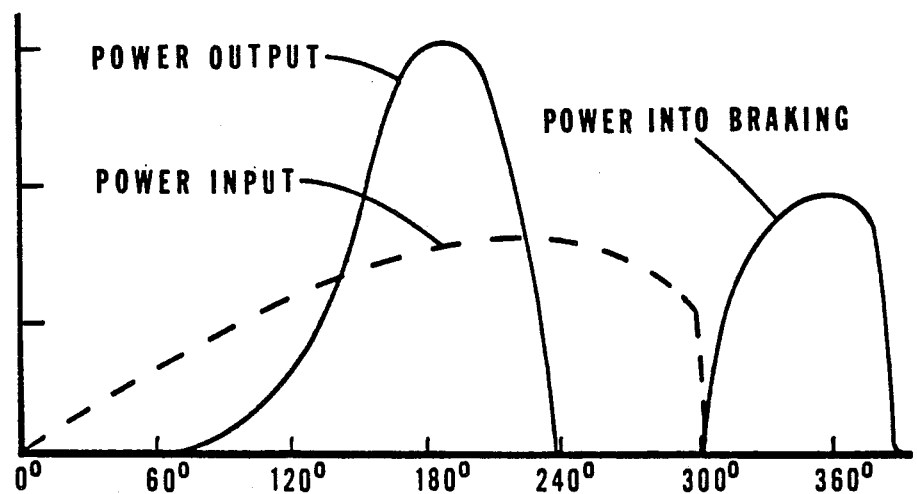
FIG. 10 shows the Power and Timing Diagram of the Loading curves for the impulse system, and the associated electrical drive pulses from the control circuitry shown in FIG. 9; which both relate to the 180 degree output characteristic of the cosine cam.
Figure 10B:
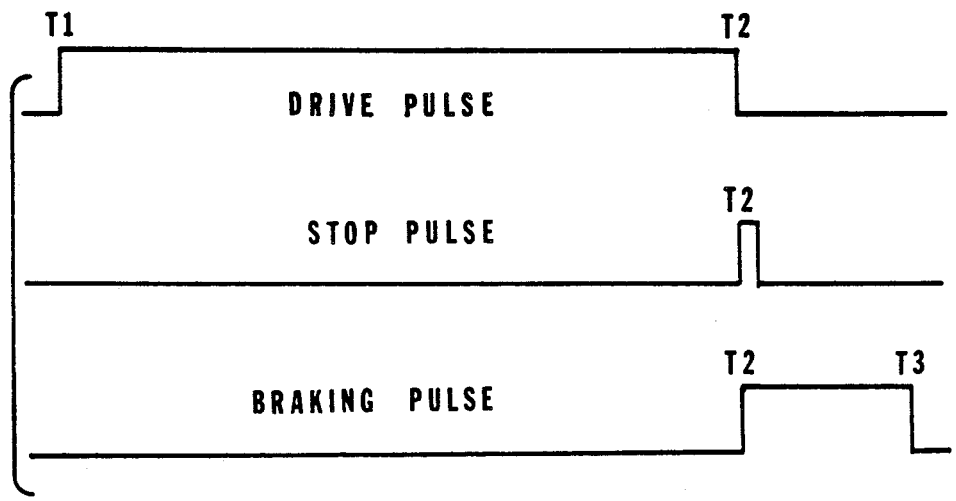

The wedding of the impulse motor, which has the power and loading curves shown in FIG. 10, and the circular cam shown in FIGS. 3 to 6, which provides the most force on the drive shaft at 180 degrees, is ideal for the fluid drop pump application shown in FIGS. 1 and 2.

The Tubular Drop Pump shown in FIGS. 1 and 2 represents a typical load for an Impulse Actuated Device. The Pump Tube 5 affords little resistance at the beginning of its compression; but then builds up to a peak compression load near the end of the compression stroke of the Bearing Shaft 2, shown in dotted lines.

With reference to the like parts numbers in both FIG. 1 and FIG. 2, the round Motor Cam 1 and Motor Timing disc 14 is set to the Shaft 12 of the D.C. Motor 13. The Motor Cam 1 freely rotates inside the Cam Bearing 3 that has a Shaft Exension 2; which, in turn, rides between the Shaft Guides 4. In both Figures the Motor Cam 1 and Bearing Shaft 2 are shown in the retracted or Start position; with the dotted lines showing the forward drive position for the Motor Cam 1B and the Pump Tube 5 in the compressed position 6.

The I.V. Tubular Pump shown in FIGS. 1 and 2 is entirely located in a short Pump Stem 7, which is located between the upper input Spike Section 11 and the lower drip chamber, which encloses the Outlet Valve 10 and its associated forward biasing Leaf Spring 10A.

The Drop Pump Tube is normally full of fluid that has entered via the Fluid Inlet 9 in the Spike Section 11, and past the Ball Valve 8. The Fluid is retained by the biasing pressure of the Leaf Spring 10A on the Outlet Valve 10. When the Tube 5 is depressed by the Bearing Shaft 2 to the Position 6 (shown by the dotted lines) the internal pressure caused by he forward stroke of the Bearing Arm 2 quickly closes the Ball Valve 8 against the valve seat at the base of the Input Aperture 9, and ejects a measured quantity of fluid through the Outlet Valve 10; by overcoming the bias pressure of the Leaf Spring 10A. The cyclic motion which produces the compression stroke to the Tube Pump 5 is shown in the sequence drawings; FIGS. 3 through 6.

THE CYCLIC SEQUENCE

Figure 3:
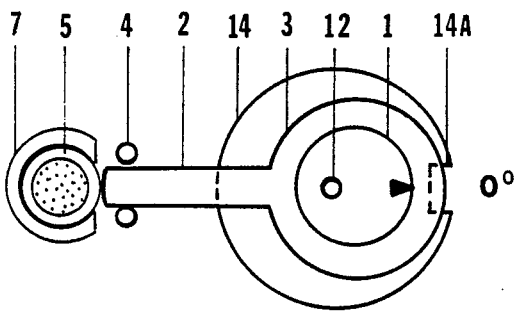

FIG. 3 shows the Motor Cam 1 in and the Bearing Shaft 2 in the normally OFF and starting position, which is at zero (0) degrees. The end of the Bearing Shaft 2 is just contacting the Pump Tube 5, which is shown in cross section. The Shaft Guide Pins 4 prevent the Shaft 2 from rotating with the Cam 1, but allow the Shaft 2 to move freely in a reciprocating motion. Both the Round Cam 1 and the Motor Timing Disc 14 are connected to the Motor Drive Shaft 12. A Notch 14A in the Timing Disc 14 is detectable by the Sensor 15.

Figure 4:
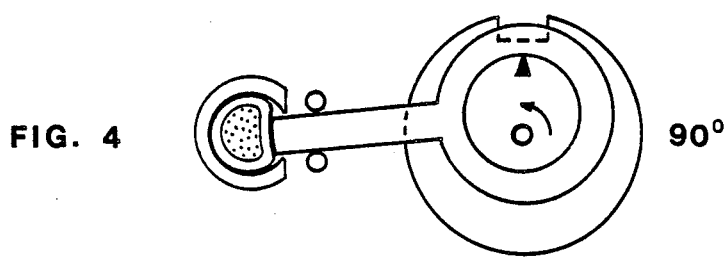

FIG. 4 shows the Motor Cam 1 and the Bearing Shaft 2 after the Motor Shaft 12 has moved through hthe first 90 degrees of rotation. Notice, at this point, that the Pump Tube 5 has just begun to be compressed, but has not yet started to become a substantial load on the motor.

Figure 5:
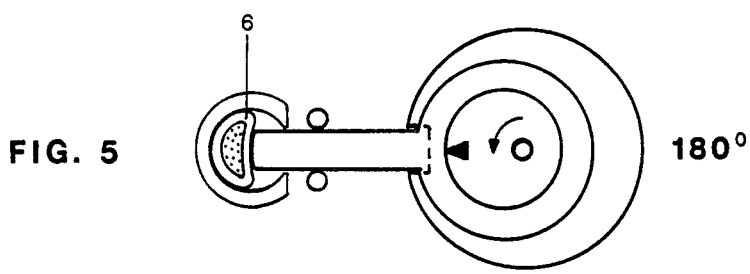

FIG. 5 shows the Cam 1 and the Cam Bearing Shaft 2 at the 180 degree point in the cycle. The Shaft 2 has reached its maxmum extension, and the Pump Tube 5 has reached its point 6 of maximum compression. As the Cam 1 moves through the top of its movement, at 180 degrees, there has been a rapidly decreasing forward movement rate, from approximately 140 degrees.

However, the maximum force from the Shaft 2 on the Pump Tube 5 is inversely proportional to the forward movement rate, consiquently, the increased power coincides with the required force curve for compressing the Pump Tube 5.

Figure 6:
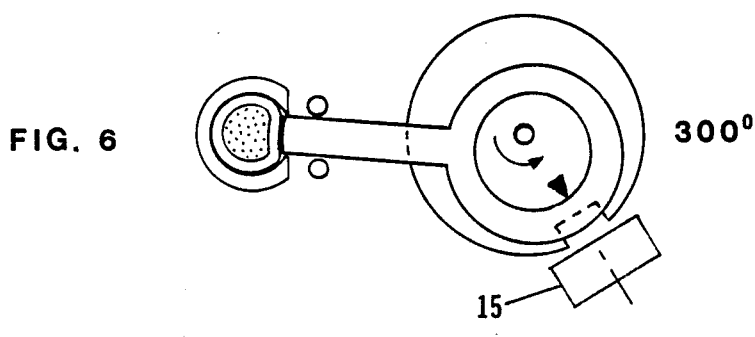

FIG. 6 shows the Cam 1 and its attached Motor Timing Disc 14 at the 300 degree point in the cycle, where the notch 14A in the Timing Disc 14 aligns with the position Sensor 15. At this time a pulse is created by the Sensor 15, which causes the associated circuitry to switch the motor to its braking mode (See FIG. 10); which results in the motor being reset to the 360 degree starting point.

THE UNIPOLAR CONTROL CIRCUITRY

Unlike many D.C. Motor control circuits, which require the reversal of polarity of all leads connected to the Motor for braking action, this new system does not require any voltage reversal circuitry. Besides avoiding the additional complexity of complete voltage reversal, the shorting-out that can occur with momentary delays during the cross-over period is avoided. FIG. 9 shows the normally-off control circuitry which requires only a single voltage supply. The Transistor Amplifier 20 acts as a switch to ground for the Drive (D) Terminal of the Motor 13, when said amplifier is turned O by the "1" Output 28 of the ON/OFF Flip Flop 27. The ON/OFF Flip Flop 27 is normally OFF between impulse cycles; until it is SET by a START pulse at the Input 29.

When the Drive Amplifier 20 is turned ON, or conducting, it (1) makes the D.C. Motor 13 start to rotate, and (2) activates the I/R Emitter Diode 17, to illuminate the Motor Timing Disc 14; and the normally positive (+) Braking Input 33 goes to ground when the I/R Detector Diode 16 conducts. As shown in FIG. 10, this start of drive point is labelled Time (T1).

The Motor 13 continues to rotate for 300 degrees in the drive mode until the Aperture 14A on the Motor Timing Disc 14 breaks the reflective light beam between the Emitter Diode 17 and the Detector Diode 16, (see FIGS. 7A, 7B and 8), at which time (T2) the Braking Input 33 goes rapidly positive (+). This rapid voltage rise is differentiated by the coupling capacitor 34 to trigger the Braking Pulse Generator 25; which is typically an Ne555 integrated circuit.

When the Output 24 of the Braking Pulse Generator 25 goes positive (+) at time (T2) two things happen simultaneously. First, the Braking Amplifier 19 is turned ON, which conducts the (B) motor terminal to ground. Second, the pulse wave-form 23 at the Output 24 is differentiated by the coupling capacitor 30 to create a positive (+) RESET pulse to the ON/OFF Flip Flop 27; which turns the Drive Amplifier 20; its associated Motor Terminal (D); and the Sensor Emitter Diode 17, OFF.

The Braking Pulse Delay Generator 25 is set to create a Braking Period (T2 to T3), which is sufficiently long to complete the braking and stabilizing of the Motor 13, with its associated Drive Cam 1 and Bearing Shaft 2, at the zero degree Start point. Reference the timing diagrams in FIG. 10.

When the Braking Period (T2 to T3) ends, the Braking Amplifier 19, with its Input Resistor 21, is turned OFF; so that all power consuming circuits are then normally off, until the next START pulse occurs. Both the ON/OFF Flip Flop 27 and the Braking Pulse Generator 25 circuits would normally be micro powered I.C. circuits, with almost negligible stand-by power.

THE MOTOR POSITION SENSING ELEMENTS

FIG. 8 shows the relationship beween the Motor Cam 1, the Cam Bearing 3, and the Bearing Shaft 2 at 300 degrees rotation. The Motor Timing Disc 14 is shown with the Timing Disc Notch 14A adjacent to the Sensor Unit Aperture 18, which causes the reflected light beam from the Emitter Diode 17 to the Detector Diode 16 to "drop out", and signal the end of the Drive Period (T1 to T2).

The relative positions of the two said diodes in the Sensor Assembly 15 is more clearly shown in FIGS. 7A and 7B. Both of the internal apertures of the emitter and detector diodes converge at equal angles through a common external Aperture 18. A section of the Timing Disc 14 is shown as a reflective surface, which directs the infra-red light beam from the Emitter Diode 17 aperture directly into the perture of the Detector Diode 16. Removal of the reflective surface (i.e. with the Notch 14A) immediately cuts off the light beam between the said diodes, and a Braking Pulse 23 is generated, as previously discussed.

It should be understood that the mechanical notch could be replaced as the means for interrupting the continuity of the reflecting surface; for example, a black non reflecting spot on the surface, etc.. In addition, the reflecting and non reflecting sections of the reflecting surface could be interchanged, with a minor change in the polarity requirements of the circuirty.

SUMMARY

All of the system elements of this invention—both mechanical and electronic—are especially well adapted to miniature and portable equipments, such as used in many medical applications. One example is the disposable I.V. Pump shown in FIG. 1 through 6. Other examples would include patient controlled injection of pain killers; digital control of anesthetic injections or air mixing; and patient worn units for automatic injection of Insulin for Diabetes, etc.. All of these devices, and others of similar nature, require a strong silent power stroke, with high power efficiency; and a normally off condition between the intermittant command pulses, to save power.

The typical size of the readily obtainable components shown in FIGS. 7, 8, and 9 are 0.50"×0.20" for the Sensor; 0.50" for the width of the Cam Bearing and Shaft; 0.60" for the width of the small D.C. Motor; and 0.75" square for the control circuitry chip.

In addition to the technical features of the Impulse Actuator System, the fact that all components are already part of mass production markets, makes the economy of manufacture an important factor in its potential future benefit to the large population requiring medical treatment. When applied to the I.V. Drop Pump example shown in the operational description, the cost advantage could be over 30 to 1 better than many of the I.V. Control Pumps that are presently being used.

The Timing disc and cosine cam configuration of the invention become invaluable in converting all of the special features of the Intermittant Single Rotation Motor Actuator, and the greatly simplified control circuitry, to efficient and functional output; for applications requiring a silent, low average power, normally off, impulse drive system.

I claim:

1. An impulse actuator system with a three pole D.C. motor which has an added brush that is electrically switched to provide a silent magnetic braking to a stop position at the end of a single rotation comprising:
    a shaft;
    a round cam having a peripheral surface connected to said shaft for rotation therewith, the connection between the cam and the shaft being off-set from the center of the cam to establish the limits of lateral motion of said peripheral surface through 180 degrees of said shaft rotation;
    a cam follower slideably connected with said peripheral surface, the connection providing for said cam and cam follower, while engaged, to slide relative to one another in a plane normal to the axis of said shaft;
    the cam follower having a cam follower arm extending radially outward and normal to the axis of said shaft;
    means connected to said housing slideably engaging said cam follower arm and providing, when said shaft is rotating, for the cam follower and its cam follower arm to have a reciprocating motion in a plane normal to the axis of said shaft; and means operatively connected to said shaft to sense the rotary position of the shaft and cam surface at between substantially 270 and 300 degrees.

2. The impulse actuator system according to claim 1 wherein said means operatively connected to said shaft comprises:

a timing disc connected to said shaft for rotation therewith, the timing disc having a peripheral reflecting surface, and a means of interrupting the continuity of the peripheral reflecting surface; and a semiconductor emitter and a semiconductor receiver mounted adjacent said timing disc reflective surface, the emitter to transmit light to said surface, which reflects same to said receiver, with said transmission being interrupted by said surface continuity interrupting means.

* * * * *